(12) United States Patent
Sumi et al.

(10) Patent No.: US 6,403,804 B1
(45) Date of Patent: Jun. 11, 2002

(54) PROCESS FOR PREPARING OPTICALLY ACTIVE OXAZOLIDINONE DERIVATIVE

(75) Inventors: Kenzo Sumi; Takashi Imai; Shigeru Mitsuhashi; Hideki Nara; Takashi Miura, all of Kanagawa (JP)

(73) Assignee: Takasago International Corporation, Tokyo (JP)

( * ) Notice: Subject to any disclaimer, the term of this patent is extended or adjusted under 35 U.S.C. 154(b) by 0 days.

(21) Appl. No.: 09/456,950

(22) Filed: Dec. 7, 1999

(30) Foreign Application Priority Data

Dec. 7, 1998 (JP) .......................................... 10-361982

(51) Int. Cl.$^7$ .......................................... C07D 263/04

(52) U.S. Cl. ........................................ 548/229; 548/232

(58) Field of Search ................................ 548/229, 232

(56) References Cited

U.S. PATENT DOCUMENTS

| | | | | |
|---|---|---|---|---|
| 4,500,717 A | * | 2/1985 | Cook et al. | .................. 548/229 |
| 4,588,694 A | * | 5/1986 | Hamaguchi et al. | ......... 435/280 |
| 4,994,602 A | | 2/1991 | Seido et al. | |
| 5,792,765 A | | 8/1998 | Riedl et al. | |
| 5,837,870 A | * | 11/1998 | Pearlman et al. | ............ 544/137 |

FOREIGN PATENT DOCUMENTS

| | | | |
|---|---|---|---|
| CA | 2028440 | | 4/1991 |
| EP | 1008 590 | * | 6/2000 |
| JP | A-2-289537 | | 11/1990 |
| WO | WO 99/52855 | | 10/1999 |

OTHER PUBLICATIONS

Shigeki Hamaguchi et al.,Asymmetric Hydrolysis of (R, S)–5 Acetoxymethyl–3–tert–butyl–oxazolidin–2–one with Enzymes and Microorganisms, Agric. Biol. Chem., 48(8), 2055–2059, 1984.
Shigeki Hamaguchi et al., Asymmetric Hydrolysis of Racemic 2–Oxazolidinone Esters with Lipases, Agric., Biol. Chem., 48(9), 2331–2337, 1984.
Shigeki Hamaguchi et al., Enzymatic Resolution of 2–Oxazolidinone Esters, Agric., Biol. Chem., 49(5), 1509–1511, 1985.
Shigeki Hamaguchi et al., Stereospecific Hydrolysis of 2–Oxazolidinone Esters and Separation of Products with an Immobilized Lipase Column, Agric., Biol. Chem., 49(6), 1661–1667, 1985.
Kazunori Kan, et al., Stereochemical Inversion of (R)–5–Hydrozymethyl–3–tert–butyl–2–oxazolidinone or (R)–5–Hydroxymethyl–3–isopropyl–2–oxazolidinone to the Corresponding (S)–Isomer, Agric., Biol. Chem., 49(6), 1669–1674, 1985.
L. D. Zhelijazkov et al., Synthese und Konfigurationsbestimmung diastereomerer 9–Methylcarbazole, Liebigs Ann. Chem. 1979, 150–161.
Jorg Oetting et al., Total synthesis of the piperidinol alkaloid(–)–(2R,3R,6S)–cassine, Tetrahedron: Asymmetry, vol. 8, No. 3., pp. 477–484, 1997.
Yasuo Fujimoto et al., Synthesis and Pharmacological Evaluation of 5–Benzyl–2–Oxazolidone Derivatives, Heterocycles, 6 (9–10) 1604–9 (1977).
Karsten Danielmeier et al., Efficient Pathways to (R)– and (S)–5–Hydroxymethyl–2–oxazolidinone and some Deriivatives, Tetrahedron: Asymmetry, vol. 6, No. 5, pp. 1181–1190, 1995.
Seiko Saito et al., One–Pot Transformation of Azido–Group to N–(t–butoxycarbonyl) Amino Group, Tetrahedron Letters, vol. 30, No. 7, pp. 837–838, 1989.
Ki–Jun Hwang et al., A Convenient Diastereoselective Synthesis of Oxazolidinone: Approach to Unusual Amino Acid Statine, Bull. Korean Chem. Soc. 1994, vol. 15, No. 7.
Walter A. Gregory et al., Antibacterials. Synthesis and Structure–Activity Studies of 3–Aryl–2–oxooxazollidines. 1. The "B" Group, J. Med. Chem. 1989, 32, 1673–1681.
Linezolid—Oxazolidinone Antibacterial, Drugs of the Future 1996, 21(11): 1116–1123.
Shohei Hashiguchi et al., Baker's Yeast Reduction of N–Protected Methyl 4–Amino–3–oxobutanoates and 3–oxopentanoates, Synthesis, Apr., 1992.
Bartjan Koning et al., New pyridine dithiols: synthesis and structures of complexes with acids, Chem. Commun. 1997.
Dieter Seebach et al., (R)–Ethyl 4–t–Butoxy–3–hydroxybutanoate, a Versatile Chiral Building Block for EPC (Enantiomerically Pure Compound) Syntheses, by Yeast Reduction of Ethyl 4–t–Butoxy–3–oxobutanoate, Synthesis Papers, Jan. 1986.

(List continued on next page.)

*Primary Examiner*—Floyd D. Higel
*Assistant Examiner*—Golam M. M. Shameem
(74) *Attorney, Agent, or Firm*—Sughrue Mion, PLLC

(57) ABSTRACT

Disclosed is a process for preparing an optically active oxazolidinone derivative comprising allowing hydrazine to react on an optically active ester having a hydroxyl group at the 3-position which is represented by formula (II):

(II)

$$\text{R}^1 \overset{\text{OH}}{\underset{*}{-}} \overset{}{\underset{R^2\ R^3}{-}} \overset{O}{\underset{}{-}} O\text{-R}^4$$

wherein $R^1$ represents a lower alkyl group having 1 to 4 carbon atoms, a phenyl group, a methoxymethyl group, a benzyloxymethyl group, a benzyloxycarbonylaminomethyl group which may have a substituent or substituents on the benzene ring thereof, an acylaminomethyl group having 3 to 10 carbon atoms, or an alkyloxycarbonylaminomethyl group having 3 to 6 carbon atoms; $R^2$ and $R^3$, which may be the same or different, each represent a hydrogen atom, a lower alkyl group having 1 to 4 carbon atoms, a phenyl group, an acetylaminomethyl group, a benzoylaminomethyl group, or a benzyl group; and * indicates an asymmetric carbon atom, and subjecting the resulting hydrazide to Curtius rearrangement.

3 Claims, No Drawings

OTHER PUBLICATIONS

Da–Ming GOU et al., A Practical Chemoenzymatic Synthesis of the Taxol C–13 Side Chain N–Benzoyl–(2R, 3S)–3–phenylisoserine, J. Org. Chem. 1993, 58, 1287–1289.

Ki–Jun Hwang,* Nam–Kyu Choi, Sung Soo Kim, and Chan–Mo Yu[1], Diastereoselective Synthesis of Oxazolidinone Derivatives and Their Antifungal Activities, Korean J. of Med. Chem., vol. 4, No. 1, 1994.

Merck Index, 12$^{th}$ Edition, 1996, pp. Misc. 68–69.

* cited by examiner

PROCESS FOR PREPARING OPTICALLY ACTIVE OXAZOLIDINONE DERIVATIVE

FIELD OF THE INVENTION

This invention relates to a process for preparing an optically active oxazolidinone derivative which is useful as a starting material for pharmaceuticals or optically active amino-alcohols.

BACKGROUND OF THE INVENTION

Optically active oxazolidinone derivatives are known as important intermediates for β-blockers (see S. Hamaguchi et al., *Agric. Biol. Chem.*, vol. 48, pp. 2055 & 2331 (1984) and idem, ibid., vol. 49, pp. 1509, 1661 & 1669 (1985)), antidepressants (e.g., JP-A-3-218367), and antibacterials (see. *Drugs Fut.*, vol. 21, p. 116 (1996) and EP 0789025A1), and an economical process of preparing them has been demanded.

Conventional processes of preparing an optically active oxazolidinone derivative include (1) a process comprising cyclizing an amino-alcohol obtained from an optically active epoxide with a dialkyl carbonate (see *J. Med. Chem.*, vol. 32, p. 1673 (1989)), (2) a process comprising ring opening of an optically active epoxide with an isocyanate or an acylazide (see *J. Med. Chem.*, vol. 32, p. 1673 (1989)), and (3) a method of synthesis starting with D-mannitol, L-ascorbic acid or (R)- or (S)-malic acid (see *Tetrahedron:Asymmetry*, vol. 6, p. 1181 (1995)).

Processes for synthesizing a racemic oxazolidinone derivative include (4) a process comprising cyclizing a β-hydroxycarboxylic acid with diphenylphosphorylazide (see *Kor. J. Med. Chem.*, vol. 4, p. 52 (1994) and *Bull. Korean Chem. Soc.*, vol. 15, p. 525 (1996)), and (5) a process comprising Curtius rearrangement of β-hydroxypropionohydrazide (see *Heterocycles*, vol. 6, p. 1604 (1977), *Tetrahedron:Asymmetry*, vol. 8, p. 477 (1997), and *Liebigs Ann. Chem.*, p. 150 (1979)).

However, these processes (1) to (5) have their several disadvantages as follows.

Process (1) (*J. Med. Chem.*, vol. 32, p. 1673 (1989)) comprises optically resolving an amino-alcohol obtained from aniline and an epoxide with optically active mandelic acid, allowing diethyl carbonate to act on the resulting optically active amino-alcohol to obtain an oxazolidinone derivative as shown below. This process has poor economical efficiency because the undesired one of the optically active amino-alcohols obtained by the optical resolution with mandelic acid is to be discarded.

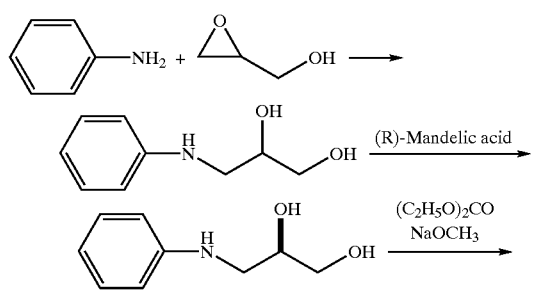

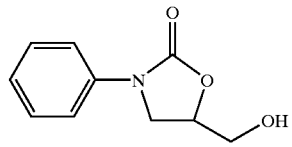

Process (2) (*J. Med. Chem.*, vol. 32, p. 1673 (1989)) comprises allowing an optically active epoxide obtained by enzymatic optical resolution to react with an isocyanate to give an optically active oxazolidinone derivative as illustrated below. The optically active epoxide used is prepared by biological resolution of an optically active $C_3$ chlorohydrin type compound, which requires a large quantity of a solvent and involves by-production of an equal amount of an unnecessary stereoisomer. Therefore, the production efficiency is low.

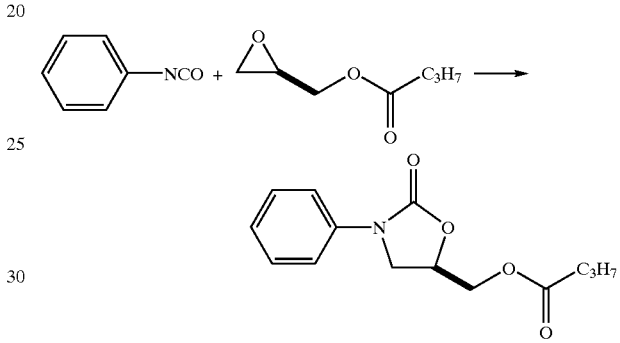

Process (3) according to *Tetrahedron:Asymmetry*, vol. 6, p. 1181 (1995) involves many steps, no matter which of D-mannitol, L-ascorbic acid, and (R)- or (S)-malic acid is used as a starting material. For example, the synthesis starting with D-mannitol proceeds as follows.

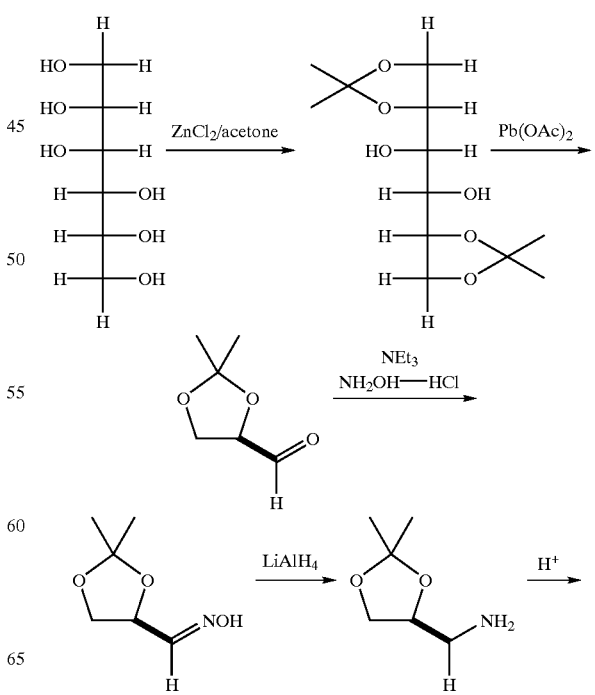

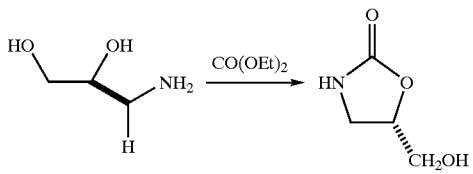

Besides requiring may steps, the process starting from D-(S)-malic acid uses diphenylphosphorylazide that is expensive.

Process (4) according to *Kor. J. Med. Chem.*, vol. 4, p. 52 (1994) comprises allowing diphenylphosphorylazide to react on β-hydroxycarboxylic acid to carry out Curtius rearrangement to obtain a racemic oxazolidinone derivative as illustrated below. As stated above, diphenylphosphorylazide is expensive. Moreover, the reaction is conducted at 80° C. at which there is a danger of explosion, which is unsuited to industrial production.

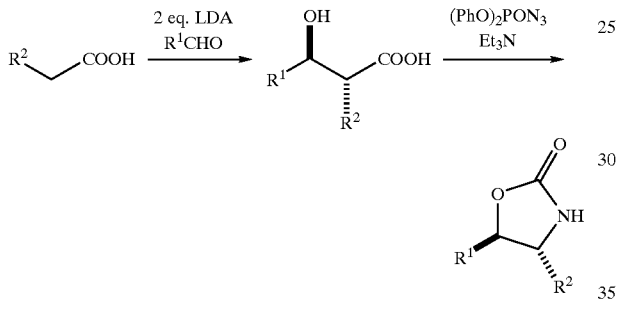

The process (4) according to *Bull. Korean Chem. Soc.*, vol. 15, p. 525 (1996) also requires expensive diphenylphosphorylazide, and the reaction is conducted at 80° C. at which there is a danger of explosion.

Process (5) (*Tetrahedron:Asymmetry*, vol. 8, p. 477 (1997)) comprises converting a β-hydroxy ester obtained by optical resolution with lipase into a hydrazide, which is subjected to Curtius rearrangement to give an optically active oxazolidinone derivative as illustrated below. According to this technique, an acylazide is produced at 5° C. or below, and the reaction system is warmed to room temperature, at which it is stirred overnight to produce a desired compound. Since the Curtius rearrangement is performed at room temperature, it needs a long time. The acylazide, being left to stand at room temperature for a long time, involves a danger of explosion, which is not suited to industrial production.

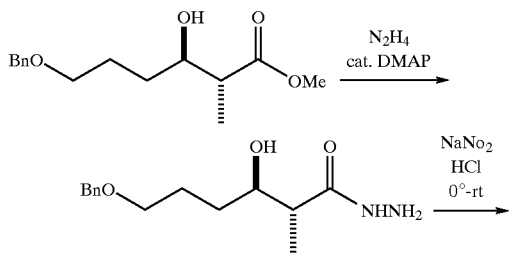

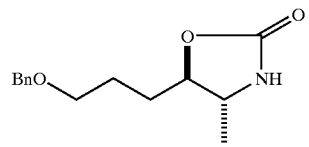

Also, in the process disclosed in *Heterocycles*, vol. 6, p. 1604 (1977) and *Liebigs Ann. Chem.*, p. 150 (1979), since a low temperature reaction system having produced an intermediate acylazide is heated to carry out the rearrangement reaction, there will be a danger of explosion where the reaction is performed on an industrial scale.

SUMMARY OF THE INVENTION

An object of the invention is to provide a novel process for obtaining an optically active oxazolidinone derivative having high optical purity in high yield without being accompanied with the above-mentioned various problems of conventional techniques.

In the light of the above circumstances, the present inventors have conducted extensive investigations, seeking for an effective and economical process for preparing an optically active oxazolidinone derivative. As a result, they have found a novel process which can achieve high optical purity and high yield with high production efficiency and no process complexity.

The invention relates to:

(1) A process for preparing an optically active oxazolidinone derivative represented by formula (I):

(I)

wherein $R^1$ represents a lower alkyl group having 1 to 4 carbon atoms, a phenyl group, a methoxymethyl group, a benzyloxymethyl group, a benzyloxycarbonylaminomethyl group which may have a substituent or substituents on the benzene ring thereof, an acylaminomethyl group having 3 to 10 carbon atoms, or an alkyloxycarbonylaminomethyl group having 3 to 6 carbon atoms; $R^2$ and $R^3$, which may be the same or different, each represent a hydrogen atom, a lower alkyl group having 1 to 4 carbon atoms, a phenyl group, an acetylaminomethyl group, a benzoylaminomethyl group, or a benzyl group; and * indicates an asymmetric carbon atom, comprising allowing hydrazine to react with an optically active acid ester having a hydroxyl group at the 3-position which is represented by formula (II):

(II)

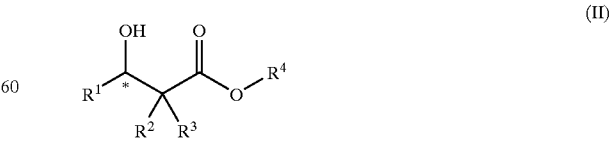

wherein $R^1$, $R^2$, $R^3$, and * are as defined above; and $R^4$ represents a lower alkyl group having 1 to 4 carbon atoms, to give an optically active hydrazide having a hydroxyl group at the 3-position which is represented by formula (III):

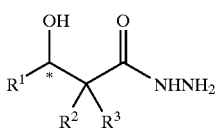

(III)

wherein $R^1$, $R^2$, $R^3$, and * are as defined above, and subjecting the optically active hydrazide to Curtius rearrangement.

(2) A process for preparing an optically active oxazolidinone derivative as set forth above, wherein the optically active hydrazide represented by formula (III) is recrystallized to increase its purity.

(3) A process for preparing an optically active oxazolidinone derivative as set forth above, wherein the optically active acid ester having a hydroxyl group at the 3-position is a compound represented by formula (II) wherein $R^1$ represents a methyl group, phenyl group, a methoxymethyl group, a benzyloxymethyl group, a benzyloxycarbonylaminomethyl group, an acetylaminomethyl group, a hexanoylaminomethyl group, or a t-butoxycarbonylaminomethyl group; $R^2$ and $R^3$ both represent a hydrogen atom, or one of $R^2$ and $R^3$ represents a hydrogen atom with the other representing an acetylaminomethyl group, a benzoylaminomethyl group, or a benzyl group; and $R^4$ represents a lower alkyl group having 1 to 4 carbon atoms.

Further, in the above-described compounds represented by formula (I) or (III), those wherein $R^1$ is an acylaminomethyl group having 3 to 10 carbon atoms or an alkyloxycarbonylaminomethyl group having 3 to 6 carbon atoms and $R^2$ and $R^3$ each represent a hydrogen atom should be novel compounds which haven't so far been known or reported. The present inventors have found that these compounds are useful as intermediates for producing pharmaceuticals or starting materials for producing optically active aminoalcohols.

In particular, the following compound represented by formula (I') is useful as an intermediate for producing linezolid (a product a Pharmacia & Upjohn, Inc.), which is useful as an antibiotic compound.

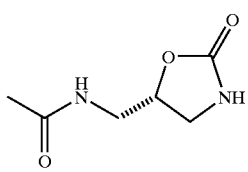

(I')

A typical production example of the above novel compounds is as follows. First, an optically active azide compound of β-hydroxylate is obtained by allowing an asymmetrically hydrogenated product of β-hydroxylate to react with sodium azide (see JP-A-8-119935). The azide compound is acylated by an ordinary method, and then is subjected to reductive rearrangement reaction to obtain an acylamide (a) (see *J. Org. Chem.*, 58, 1287 (1993)). Alternatively, the above obtained azide compound is subjected to reductive rearrangement reaction in the co-presence of di-tert-butyldicarbonate ((Boc)$_2$O) to obtain an optically active β-hydroxylate where an amino group is protected (b) (see *Tetrahedron Lett.*, 30, 837 (1989)). The above obtained acylamide (a) or hydroxylate (b) is allowed to act on a hydrazine, and then the resulting compound is subjected to Curtius rearrangement to obtain a novel optically active oxazolidinone compound.

DETAILED DESCRIPTION OF THE INVENTION

The optically active ester derivative having a hydroxyl group at the 3-position represented by formula (II), which can be used as a starting compound, is prepared by asymmetric hydrogenation of a β-keto ester represented by formula (IV):

(IV)

wherein $R^1$, $R^2$, $R^3$, and $R^4$ are as defined above.

The β-keto ester of formula (IV) wherein $R^1$ is a lower alkyl group having 1 to 4 carbon atoms or a phenyl group is synthesized from an easily available 3-ketobutyric ester (acetoacetic ester) in a known manner, for example by the reaction between an acetoacetic ester and an acid halide as taught in JP-A-10-53561. The β-keto ester of formula (IV) wherein $R^1$ is a methoxymethyl group or a benzyloxymethyl group (i.e., a 4-alkoxy-3-oxybutyric ester) is synthesized from an easily available 4-halogeno-3-oxopropionic ester in a known manner, for example the process disclosed in R. M. Kellogg et al., *J. Chem. Soc., Chem. commun.*, p. 932 91997) or D. Seebach et al., *Synthesis*, p. 37 (1986). The β-keto ester of formula (IV) wherein $R^1$ is a group carrying an aminomethyl moiety having a protective group on its nitrogen atom (i.e., a benzyloxycarbonylaminomethyl group) is synthesized from, for example, easily available benzyloxycarbonylglycine in a known manner, for example, the process disclosed in Natsugari et al., *Synthesis*, p. 403 (1992).

Where $R^1$ in the β-keto ester of formula (IV) is a benzyloxycarbonylaminomethyl group, an acylaminomethyl group, or an alkyloxycarbonylaminomethyl group, the benzyl moiety of the amino protective group may have one or more substituents. Examples of the substituents include a lower alkyl group having 1 to 4 carbon atoms (preferably methyl or t-butyl), a lower alkoxy group having 1 to 4 carbon atoms (preferably methoxy), a halogen atom (e.g., chlorine). Examples of the substituted benzyl group are p-methoxybenzyl, 2,4-dimethoxybenzyl, p-methylbenzyl, 3,5-dimethylbenzyl, p-chlorobenzyl, and p-t-butylbenzyl.

Examples of the acyl group are acetyl, propanoyl, butanoyl, pentanoyl, hexanoyl, heptanoyl, octanoyl, nonanoyl, and decanoyl.

Examples of the alkyloxycarbonyl group are methoxycarbonyl, ethoxycarbonyl, propoxycarbonyl, butoxycarbonyl, and t-butoxycarbonyl.

The β-keto ester of formula (IV) which has a substituent (s) at the 2-position, for example where $R^2$ and/or $R^3$ is an acetylaminomethyl group, a benzoylaminomethyl group, or a benzyl group can be synthesized according to the process described in JP-A-2-231471.

Asymmetric hydrogenation of the β-keto ester of formula (IV) can be conveniently carried out in accordance with the method of JP-A-2-289537. That is, the reaction is conducted in an alcohol solvent in the presence of a catalytic amount of a ruthenium-optically active phosphine complex under a hydrogen pressure of 500 to 10000 Kpa at 10 to 100° C. for 5 to 20 hours.

The ruthenium-optically active phosphine complex which is preferably used includes the complex described in JP-61-63690 which is represented by formula (V):

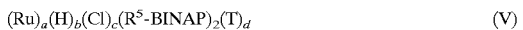

$(Ru)_a(H)_b(Cl)_c(R^5\text{-BINAP})_2(T)_d$ (V)

wherein $R^5$-BINAP represents a tertiary phosphine represented by formula (VI):

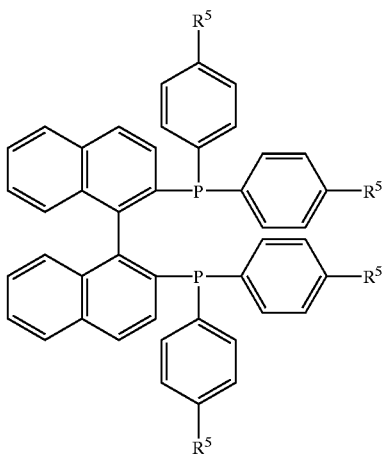

(VI)

$R^5$ represents a hydrogen atom, a methyl group, a t-butyl group or a methoxy group; T represents a tertiary amine; b represents 0 or 1; when b is 0, a is 2, c is 4, and d is 1; and when b is 1, a is 1, c is 1, and d is 0, and the complex described in JP-A-62-265293 which is represented by formula (VII):

(VII)

wherein $R^5$-BINAP is as defined above; and $R^6$ represents a lower alkyl group having 1 to 4 carbon atoms or a trifluoromethyl group.

The tertiary phosphine ($R^5$-BINAP) of formula (VI) specifically includes 2,2'-bis(diphenylphosphino)-1,1'-binaphthyl (hereinafter referred to as BINAP), 2,2'-bis[di(p-tolyl) phosphino]-1,1'-binaphthyl (hereinafter referred to as Tol-BINAP), 2,2'-bis[di(p-t-butylphenyl) phosphino]-1,1'-binaphthyl (hereinafter referred to as t-Bu-BINAP), and 2,2'-bis[di(p-methoxyphenyl) phosphino]-1,1'-binaphthyl (hereinafter referred to as Methoxy-BINAP).

These tertiary phosphines of formula (VI) each take a (+)-form or (−)-form, which is selected in agreement with the absolute configuration of a desired optically active compound of formula (II). That is, a (+)-form is chosen for obtaining a (3R)-compound; and a (−)-form for a (3S)-compound.

The tertiary amine (T) in formula (V) includes triethylamine, tributylamine, ethylisopropylamine, 1,8-bis(dimethylamino) naphthalene, dimethylaniline, pyridine, and N-methylpiperidine, with triethylamine being preferred.

The following complexes 1 to 8 are examples of the complex represented by formula (V) and complexes 9 through 16 are examples of the complex represented by formula (VII), in which representation of the absolute configuration of the tertiary phosphine is omitted. "Et" stands for an ethyl group; "Tol", a tolyl group; and "t-Bu" a t-butyl group.

Complex 1: $Ru_2Cl_4(BINAP)_2NEt_3$
Complex 2: $Ru_2Cl_4(tol-BINAP)_2NEt_3$
Complex 3: $Ru_2Cl_4(t-Bu-BINAP)_2NEt_3$
Complex 4: $Ru_2Cl_4(Methoxy-BINAP)_2NEt_3$
Complex 5: $RuHCl(BINAP)_2$
Complex 6: $RuHCl(Tol-BINAP)_2$
Complex 7: $RuHCl(T-Bu-BINAP)_2$
Complex 8: $RuHCl(Methoxy-BINAP)_2$
Complex 9: $Ru(BINAP)(O_2CCH_3)_2$
Complex 10: $Ru(Tol-BINAP)(O_2CCH_3)_2$
Complex 11: $Ru(t-Bu-BINAP)(O_2CCH_3)_2$
Complex 12: $Ru(Methoxy-BINAP)(O_2CCH_3)_2$
Complex 13: $Ru(BINAP)(O_2CCF_3)_2$
Complex 14: $Ru(Tol-BINAP)(O_2CCF_3)_2$
Complex 15: $Ru(T-Bu-BINAP)(O_2CCF_3)_2$
Complex 16: $Ru(Methoxy-BINAP)(O_2CCF_3)_2$ The ruthenium-optically active phosphine complex is used in an amount of $1/100$ to $1/10000$ mol, preferably $1/500$ to $1/4000$ mol, per mole of the β-keto ester, the substrate of asymmetric hydrogenation. The asymmetric hydrogenation is conveniently carried out in an alcohol solvent, particularly methyl alcohol, ethyl alcohol or isoporopyl alcohol. Ethyl alcohol is the most preferred solvent. The amount of the solvent to be used is usually 1 to 5 times (by volume/weight) the substrate.

The optically active hydrazide represented by formula (III) is synthesized by allowing hydrazine to react on the optically active acid ester represented by formula (II), which is prepared by the above-described asymmetric hydrogenation, in an alcohol solvent. The reaction usually proceeds at 0 to 100° C., preferably 30 to 70° C.

Preferred alcohol solvents include methyl alcohol, ethyl alcohol, and isopropyl alcohol. Hydrazine is used in an amount of 1 to 5 mol, preferably 1.1 to 1.5 mol, per mole of the compound of formula (II). After completion of the reaction, the resultant crude optically active hydrazide is purified by recrystallization from methanol containing isopropyl alcohol and filtered to give an optically active hydrazide having a hydroxyl group at the 3-position as represented by formula (III) having optical purity in a high yield.

In the final stage of the process of the invention, Curtius rearrangement is effected on the optically active hydrazide of formula (III) to give an optically active oxazolidinone derivative of formula (I).

Unlike the process taught by the literature, P.A.S. Smith, *Organic Reactions*, vol. 11, p. 337 (1946), the Curtius rearrangement applied to the invention is performed by allowing sodium nitrite to react on the optically active hydrazide having a hydroxyl group at the 3-position as represented by formula (III) in the presence of an acid to once produce an intermediate acyl azide, and allowing the reaction mixture as containing the acyl azide to stand or adding the reaction mixture dropwise to a heated solvent, thereby to yield the desired optically active oxazolidinone derivative of formula (I) in a safe manner.

The amount of sodium sulfite to be used ranges 1 to 2 mols, preferably 1.1 to 1.3 mols, per mole of the hydrazide (III). The acid which can be used in the Curtius rearrangement as intended in the invention includes hydrochloric acid, sulfuric acid, phosphoric acid, acetic acid, sulfonic acid, methanesulfonic acid, and p-toluenesulfonic acid. Preferred of them are hydrochloric acid, sulfuric acid, and acetic acid. Solvents which can be used in the reaction include halogenated hydrocarbons, such as methylene chloride and chloroform; ketones, such as acetone; esters, such as ethyl acetate and butyl acetate; ethers, such as diethyl ether and diisopropyl ether; alcohols, such as methanol, ethanol, and butanol; hydrocarbons, such as hexane, heptane, toluene, and benzene; water; and mixtures thereof. Water or a mixed solvent of water and an ether is particularly preferred. The reaction temperature ranges from 20 to 100° C., preferably from 30 to 50° C. According to the process of the invention, the stereoisomerism of the optically active hydrazide of formula (III) can be retained throughout the Curtius rearrangement to give the desired optically active oxazolidinone derivative of formula (I) having the desired stereoisomerism.

The present invention provides a novel process of producing an optically active oxazolidinone derivative at high production efficiency with no process complexity. The invention also provides a novel process of producing an optically active oxazolidinone derivative having high optical purity in high yield.

The invention will now be illustrated in greater detail with reference to Reference Examples and Examples, but it should be understood that the invention is not limited thereto. Measurement of physical properties in Examples was made with the following instruments unless otherwise specified.

1) Nuclear magnetic resonance (NMR) spectrum
    A. $^2$H-NMR: Gemini 200 (200 MHz), manufactured by Varian, Inc. DRX500 (500 MHz), manufactured by Bruker Japan, Co., Ltd.
    Internal standard: tetramethylsilane
    B. $^{13}$C-NMR: Gemini 200 (50 MHz), manufactured by Varian, Inc. DRX500 (126 MHz), manufactured by Bruker Japan, Co., Ltd.
    Internal standard: tetramethylsilane
2) Melting point
    MP-S3, available from Yanagimono Shoji K. K.
3) High-performance liquid chromatography (HPLC)
    Liquid Chromatograph L-600, manufactured by Hitachi, Ltc.
4) Gas chromatography (GC)
    5890-II, manufactured by Hewlett Packard The product was led to its MTPA ester or MTPA amide for determination of the optical purity, wherein MTPA stands for (R)- or (S)-α-methoxy-α-(trifluoromethyl)phenylacetic acid.

REFERENCE EXAMPLE 1

Synthesis of Methyl (R)-4-Methoxy-3-Hydroxybutyrate:

In a 2 liter four-necked flask were charged 88.0 g (2.2 mol) of 60% sodium hydride and 753 ml of tetrahydrofuran in a nitrogen stream, and a mixture of 150.6 g (1.0 mmol) of methyl 4-chloro-3-oxo-butyrate and 35.2 g (1.1 mol) of methanol was added thereto dropwise at room temperature (22 to 24° C.). After the addition, the mixture was stirred at room temperature (22 to 24° C.) for 1 hour. The reaction mixture was cooled with ice, and 600 ml (1.2 mol) of 2N hydrochloric acid was added dropwise. The tetrahydrofuran was recovered from the reaction mixture, and 400 ml of toluene was added to the residue. The aqueous phase was extracted with three 200 ml portions of toluene. The organic phase was washed with a 5% sodium chloride aqueous solution, and the solvent was evaporated under reduced pressure. The residue was distilled under reduce pressure (boiling point: 90° C./1000 Pa) to give 107.7 g (74%) of methyl 4-methoxy-3-oxobutyrate as liquid.

$^1$H-NMR (200 MHz, CDCl$_3$, δ ppm): 4.08 (s, 2H), 3.74 (s, 3H), 3.52 (s, 2H), 3.42 (s, 3H)

In a 10 liter autoclave were put 1473 g (10.08 mol) of methyl 4-methoxy-3-oxobutyrate, 2210 ml of ethanol, and 4.59 g (5.09 mmol) of Ru$_2$Cl$_4$((S)-Tol-BINAP)$_2$.NEt$_3$, and asymmetric hydrogenation was carried out at 100° C. under a hydrogen pressure of 4000 kPa for 4 hours (conversion: 100%). The solvent was removed by evaporation to yield 1490 g of the title compound as liquid.

$^1$H-NMR (200 MHz, CDCl$_3$, δ ppm): 4.3–4.1 (m, 1H), 3.70 (s, 3H), 3.42 (dd, J=4.6, 12.2 Hz, 1H), 3.36 (dd, J=6.0, 12.2 Hz, 1H), 3.38 (s, 3H), 2.52 (d, J=6.4 Hz, 2H).

Optical purity was measured as follows. The resultant compound was lead to its (R)-MTPA ester, which was analyzed by HPLC under the following conditions to find the optical purity to be 95%e.e.

Column: Cosmosil 5SL (4.6 mm×250 mm), produced by Nacalai Tesque Inc.

Solvent: hexane/diethyl ether=3/1 (by volume)

Flow rate: 1.0 ml/min

Detection: 254 nm

EXAMPLE 1

Synthesis of (R)-4-methoxy-3-hydroxybutanohydrazide

In a 10 liter four-necked flask were charged 1036 g (6.99 mol) of methyl (R)-4-methoxy-3-hydroxybutyrate (optical purity: 94%e.e.) and 4140 ml of ethanol in a nitrogen stream, and 525 g (10.49 mol) of hydrazine monohydrate was added thereto at room temperature over 20 minutes, followed by stirring at 70° C. for 6 hours. The reaction mixture was cooled to room temperature (22 to 24° C.), and 2 liter of isopropyl alcohol was added, followed by cooling to 5° C., at which the reaction mixture was stirred for 1 hour. The precipitate thus formed was filtered and washed with 0.45 liter of isopropyl alcohol to collect 626.5 g of first crystals. To the first mother liquor were added 1 liter of methanol and 0.5 liter of isopropyl alcohol, followed by crystallization in the same manner as above to give 225.2 g of second crystals. The combined first and second crystals weighed 851.7 g (82%). Melting point: 101.4° C. Optical purity: >99.9%e.e.

$^1$H-NMR (200 MHz, CD$_3$OD, δ ppm): 4.2–4.0 (m, 1H), 3.4–3.2 (m, 2H), 3.37 (s, 3H), 2.37 (dd, J=5.0, 14.2 Hz, 1H), 2.20 (dd, J=7.7, 14.2 Hz, 1H)

The optical purity of the product was measured as follows. An acetic acid solution (1 ml) of 40 mg (0.27 mmol) of the resulting (R)-4-methoxy-3-hydroxybutanohydrazide was cooled to 5° C., and 28 mg (0.40 mmol) of sodium nitrite was added. The reaction mixture was stirred at room temperature (22 to 24° C.) for 1 hour and then heated up to 80° C., at which the mixture was further stirred for 1 hour. The acetic acid was removed by evaporation under reduced pressure. The optical purity of the resulting crude product was measured by gas chromatography under the following conditions.

Column: ALPHA DEX 120 (0.25 mm×30 mm), manufactured by SUPELCO.

Injection temperature: 200° C.

Column temperature: 100 to 250° C.

Detection temperature: 250° C.

Rate of temperature rise: 5° C./min

EXAMPLE 2

Synthesis of (R)-5-methoxymethyl-2-oxazolidinone

In a 500 ml four-necked flask were charged 100.0 g (0.675 mol) of the (R)-4-methoxy-3-hydroxybutanohydrazide obtained in Example 1 (optical purity: >99.9%e.e.) and 150 ml of water in a nitrogen stream, and 64.5 ml (0.742 mol) of 35% concentrated hydrochloric acid was added thereto dropwise under cooling with ice (0 to 5° C.) over a period of 35 minutes. After the addition, 130 ml of an aqueous solution containing 51.2 g (0.742 mol) of sodium nitrite was added thereto under ice-cooling (0 to 5° C.) over a period of 2 hours and 25 minutes. After the addition, the mixture was stirred under ice-cooling (0 to 5° C.) for 1 hour. Separately, 100 ml of water was put in a 1 liter 4-necked flask and heated to 50° C. in a nitrogen stream. The reaction mixture prepared above was dropped into the flask over 2 hours and 10 minutes. During the dropwise addition, nitrogen gas was evolved violently, and the reaction temperature rose to 55° C. The resulting reaction mixture was stirred at 50° C. for 2 hours. Water was evaporated under reduced pressure, and 100 ml of methanol was added to the residue, followed by filtration to remove sodium chloride. Methanol was removed from the mother liquor by evaporation under reduced pressure, and 100 ml of methanol was added to the residue, followed by filtration to remove sodium chloride. Methanol was removed from the mother liquor by evaporation under reduced pressure, and the residue was distilled under reduced pressure (141° C./100 Pa.) to give 81.1 g (92%) of the title compound. Optical purity: 99.9%e.e. or higher.

$^1$H-NMR (200 MHz, CDCl$_3$, δ ppm): 4.76 (ddt, J=6.6, 8.8, 4.8 Hz, 1H), 3.66 (ddd, J=8.8, 8.4, 4.4 Hz, 1H), 3.59 (d, J=4.8 Hz, 1H), 3.50 (ddd, J=6.6, 8.4, 1.0 Hz, 1H), 3.43 (s, 3H)

$^{13}$C-NMR (50 MHz, CDCl$_3$, δ ppm): 159.96, 72.59, 59.04, 42.09

Measurement of the optical purity of the product was made by gas chromatography under the following conditions.

Column: ALPHA DEX 120 (0.25 mm×30 m), manufactured by SUPELCO.

Injection temperature: 200° C.

Column temperature: 100° to 250° C.

Detection temperature: 250° C.

Rate of temperature rise: 5° C./min

REFERENCE EXAMPLE 2

Synthesis of ethyl (S)-4-benzyloxy-3-hydroxybutyrate

A mixture of 112 g (1.04 mol) of benzyl alcohol and 155 g (0.94 mol) of ethyl 4-chloro-3-oxobutyrate was added dropwise to a suspension of 82.9 g (2.07 mol) of 60% sodium hydride in 775 ml of tetrahydrofuran at 35 to 40° C. After the addition, the reaction mixture was stirred at 40° C. for 1 hour. Tetrahydrofuran was recovered from the reaction mixture, and 500 ml of heptane was added to the residue. The resulting solution was added dropwise to 800 ml of water to precipitate crystals, which were separated at room temperature and washed with heptane. To the crystals were added 800 ml of butyl acetate and 1000 ml of 1N hydrochloric acid to conduct extraction. The organic phase was washed successively with 500 ml of a 5% sodium chloride aqueous solution, 500 ml of a 5% sodium hydrogencarbonate aqueous solution, and 500 ml of a 5% sodium chloride aqueous solution to adjust the pH to 6 to 7. Butyl acetate was recovered, and 100 ml of heptane was added to the residue. The mixture was stirred, followed by liquid-liquid separation to obtain 173 g (78%) of ethyl 4-benzyloxy-3-oxobutyrate.

$^1$H-NMR (200 MHz, CDCl$_3$, δ ppm): 7.6–7.2 (m, 5H), 5.16 (s, 2H), 4.15 (q, J=7.2 Hz, 2H), 3.45 (s, 2H), 1.21 (t, J=7.2 Hz, 3H)

In a 100 ml autoclave were charged 20.0 g (84.7 mmol) of ethyl 4-benzyloxy-3-oxobutyrate, 16 ml of ethanol, and 31 mg (0.034 mmol) of Ru$_2$Cl$_4$((R)-Tol-BINAP)$_2$.NEt$_3$, and asymmetric hydrogenation was performed at 100° C. under a hydrogen pressure of 10 torr for 3 hours (conversion: 100%). The solvent was evaporated under reduced pressure to give 18.0 g of the title compound as liquid.

$^1$H-NMR (200 MHz, CDCl$_3$, δ ppm): 7.4–7.2 (m, 5H), 4.56 (s, 2H), 4.3–4.1 (m, 1H), 4.15 (q, J=7.1 Hz, 2H), 3.53 (dd, J=4.6, 9.5 Hz, 1H), 3.46 (dd, J=5.9, 9.5 Hz, 1H), 3.00 (bs, 1H), 2.54 (d, J=6.2 Hz, 2H), 1.25 (t, J=7.1 Hz, 3H).

The product was led to its (R)-MTPA ester, which was analyzed by HPLC under the following conditions to find the optical purity to be 89%e.e.

Column: Cosmosil 5SL (4.6 mm×250 mm), produced by Nacalai Tesque Inc.

Solvent: hexane/diethyl ether=9/1 (by volume)

Flow rate: 1.0 ml/min

Detection: 254 nm

EXAMPLE 3

Synthesis of (S)-4-benzyloxy-3-hydroxybutanohydrazide

In a 100 ml flask were put 4.15 g (17.4 mmol) of ethyl (S)-4-benzyloxy-3-hydroxybutyrate (optical purity: 89%e.e.) prepared in Reference Example 2, 20 ml of ethanol, and 2.62 g (52.2 mmol) of hydrazine monohydrate in a nitrogen stream, and the mixture was heated under reflux for 20 hours. The reaction mixture was cooled to room temperature (22 to 24° C.), and ethanol was removed by evaporation under reduced pressure. To the residue was added 40 ml of diethyl ether, followed by heating under reflux to dissolve the crude crystals. The solution was cooled to 5° C., followed by stirring for 1 hour. The crystals thus precipitated were collected by filtration and washed with 10 ml of diethyl ether to give 2.90 g (74%) of the title compound. Melting point: 96.9° C. Optical purity: >99.9%e.e.

$^1$H-NMR (200 MHz, CDCl$_3$, δ ppm): 7.4–7.2 (m, 5H), 4.56 (s, 2H), 4.3–4.1 (m, 1H), 4.0–3.8 (bs, 2H), 3.51 (dd, J=4.6, 9.6 Hz, 1H), 3.44 (dd, J=6.4, 9.4 Hz, 1H), 2.41 (dd, J=4.8, 15.4 Hz, 1H), 2.31 (dd, J=7.4, 15.4 Hz, 1H), 1.8–1.5 (bs, 1H).

The measurement of the optical purity of the product was made as follows. An acetic acid solution (1 ml) of 50 mg (0.22 mol) of the resulting (S)-4-benzyloxy-3-hydroxybutanohydrazide was cooled to 5° C., and 23 mg (0.33 mmol) of sodium nitrite was added. The reaction mixture was stirred at room temperature (22 to 24° C.) for 1 hour and then heated up to 80° C., at which the mixture was further stirred for 1 hour. The acetic acid was removed by evaporation under reduced pressure. The resulting crude product was led to its (R)-MTPA amide derivative and analyzed by HPLC under the following conditions.

Column: Cosmosil 5SL (4.6 mm×250 mm), produced by Nacalai Tesque Inc.

Solvent: hexane/diethyl ether=3/7 (by volume)

Flow rate: 1.0 ml/min

Detection: 254 nm

EXAMPLE 4

Synthesis of (S)-5-benzyloxymethyl-2-oxazolidinone

In a 20 ml two-necked flask were put 150 mg (0.67 mmol) of the (S)-4-benzyloxy-3-hydroxybutanohydrazide (optical purity: >99.9%e.e.) obtained in Example 3 and 2 ml of water in a nitrogen stream, and 85 ml (1.01 mmol) of 35% concentrated hydrochloric acid was added thereto over 3 minutes while cooling with ice (0 to 5° C.). After the dropwise addition, while cooling with ice (0 to 5° C.), 1 ml of diethyl ether was added thereto, and 69 mg (1.01 mmol) of sodium nitrite was then added over 3 minutes. After stirring under ice-cooling (0 to 5° C.) for 1 hour, 1 ml of a saturated aqueous solution of sodium hydrogencarbonate was added to the reaction mixture, and the mixture was extracted with 10 ml of butyl acetate. The organic phase was washed with 2 ml of a 5% aqueous solution of sodium chloride. Separately, 1 ml of butyl acetate was put in a 20 ml two-necked flask and heated to 100° C. in a nitrogen stream, and the above prepared butyl acetate extract was added thereto dropwise over 10 minutes. Meanwhile nitrogen gas was evolved vigorously. The reaction mixture was stirred at 100° C. for 4 hours. Butyl acetate was removed by evaporation under reduced pressure, and the residue was purified by column chromatography to afford 137 mg of the title compound in a yield of 99%. Optical purity: 99.9%e.e. or higher.

$^1$H-NMR (200 MHz, CDCl$_3$, δ ppm): 7.4–7.2 (m, 5H), 6.6–6.4 (m, 1H), 4.9–4.6 (m, 1H), 4.58 (s, 2H), 3.61 (dd, J=8.0, 8.4 Hz, 1H), 3.62 (d, J=4.8 Hz, 2H), 3.42 (dd, J=6.6, 8.4 Hz, 1H).

Measurement of the optical purity was made by converting the product to its (R)-MTPA amide derivative and analyzing the amide compound by HPLC under the following conditions.

Column: Cosmosil 5SL (4.6 mm×250 mm), produced by Nacalai Tesque Inc.
Solvent: hexane/diethyl ether=3/7 (by volume)
Flow rate: 1.0 ml/min
Detection: 254 nm

REFERENCE EXAMPLE 3

Synthesis of ethyl (S)-4-benzyloxycarbonylamino-3-hydroxybutyrate

In a 1 liter four-necked flask were charged 50 g (0.24 mol) of N-benzyloxycarbonylglycine and 300 ml of acetonitrile in a nitrogen stream, and 39.5 g (0.24 mol) of 1,1'-carbonyldiimidazole was added thereto over 30 minutes, followed by stirring at room temperature (22 to 24° C.) for 2 hours. After cooling to 7° C., 61.0 g (0.36 mol) of potassium malonate ethyl ester was added over 5 minutes, and 23.0 g (0.24 mol) of magnesium chloride was added over 30 minutes, followed by stirring at room temperature for 30 minutes and then at 50° C. for 2 hours to complete the reaction. Acetonitrile was removed by evaporation under reduced pressure, and 550 ml of a 5% hydrochloric acid aqueous solution was added to the reaction. The mixture was extracted and washed with 180 ml of butyl acetate. The organic layer was further washed with 100 ml of a 5% hydrochloric acid aqueous solution, neutralized with 100 ml of a 8% sodium carbonate aqueous solution, and washed with 100 ml of water. The solvent was removed by evaporation under reduced pressure to yield 67.1 g (90% as purified by column chromatography) of ethyl 4-benzyloxycarbonylamino-3-oxobutyrate as liquid.

$^1$H-NMR (200 MHz, CDCl$_3$, δ ppm): 7.4–7.2 (m, 5H), 5.63 (s, 1H), 5.10 (s, 2H), 4.1–4.2 (m, 4H), 3.46 (s, 2H), 1.26 (t, J=7.1 Hz, 3H)

In a 200 ml autoclave were charged 40 g (0.13 mol) of ethyl 4-benzyloxycarbonylamino-3-oxobutyrate, 120 ml of ethanol, and 173 mg (0.102 mmol) of Ru$_2$Cl$_4$((R)-Tol-BINAP)$_2$.NEt$_3$, and asymmetric hydrogenation was carried out at 50° C. under a hydrogen pressure of 30 torr. for 17 hours (conversion: 98.4%; optical purity: 94%e.e.). Ethanol was evaporated under reduced pressure to furnish 38.9 g of the title compound as liquid. An aliquot of the product was purified to find that the yield was 91%.

$^1$H-NMR (200 MHz, CDCl$_3$, δ ppm): 7.4–7.2 (m, 5H), 5.48 (s, 1H), 5.09 (s, 2), 4.2–4.0 (m, 4H), 3.4–3.1 (m, 2H), 2.5–2.4 (m, 2H), 1.26 (t, J=7.1 Hz, 3H)

The measurement of the optical purity was made under the following conditions.

Column: Chiralcel OD-H (4.6 mm×250 mm), manufactured by Daicel Chemical Industries, Ltd.
Solvent: hexane/isopropyl alcohol=9/1 (by volume)
Flow rate: 1.0 ml/min
Detection: 210 nm

EXAMPLE 5

Synthesis of (S)-benzyloxycarbonylamino-3-hydroxybutanohydrazide

In a 100 ml flask were charged 2.70 g (9.60 mmol) of the ethyl (S)-4-benzyloxycarbonylamino-3-hydroxybutyrate (optical purity: 94%e.e.) prepared in Reference Example 3, 40 ml of ethanol, and 2.40 g (48.0 mmol) of hydrazine monohydrate in a nitrogen stream, followed by heating under reflux for 20 hours. The reaction mixture was cooled to room temperature (22 to 24° C.), and ethanol was evaporated under reduced pressure. To the residue was added 30 ml of methanol and heat-refluxed to dissolve the crude crystals, followed by cooling to 5° C. After stirring for 1 hour for crystallization, the precipitated crystals were collected by filtration and washed with 10 ml of diethyl ether to afford 1.42 g (52%) of the title compound. Melting point: 135.4° C. Optical purity: >99.9%e.e.

$^1$H-NMR (200 MHz, CD$_3$OD, δ ppm): 7.4–7.2 (m, 5H), 5.07 (s, 2H), 4.2–3.9 (m, 1H), 3.22 (dd, J=5.4, 14.0 Hz, 1H), 3.13 (dd, J=6.3, 14.0 Hz, 1H), 2.32 (dd, J=4.8, 14.4 Hz, 1H), 2.21 (dd, J=8.2, 14.4 Hz).

The optical purity of the product was determined as follows. An acetic acid solution (1 ml) of 50 mg (0.19 mmol) of the (S)-4-benzyloxycarbonylamino-3-hydroxybutanohydrazide was cooled to 5° C., and 19 mg (0.28 mmol) of sodium nitrite was added to the solution. The reaction mixture was stirred at room temperature (22 to 24° C.) for 1 hour, followed by heating to 80° C., at which the reaction mixture was stirred for 1 hour. The acetic acid was removed by evaporation under reduced pressure, and the crude product was converted to an (R)-MTPA amide derivative, which was analyzed by HPLC under the following conditions.

Column: Cosmosil 5SL (4.6 mm×250 mm), produced by Nacalai Tesque Inc.
Solvent: hexane/diethyl ether=3/7 (by volume)
Flow rate: 1.0 ml/min
Detection: 254 nm

EXAMPLE 6

Synthesis of (R)-5-benzyloxycarbonylaminomethyl-2-oxazolidinone

In a 20 ml two-necked flask were put 103 mg (0.39 mmol) of the (S)-4-benzyloxycarbonylamino-3- hydroxybutanohydrazide (optical purity: >99.9%e.e.) obtained in Example 5 and 1 ml of water in a nitrogen stream, and 49 ml (0.59 mmol) of 35% concentrated hydrochloric acid was added thereto over 3 minutes while cooling with ice (0 to 5° C.). After the dropwise addition, while cooling with ice (0 to 5° C.), 1 ml of diisopropyl ether was added thereto, and 40 mg (0.59 mmol) of sodium nitrite was then added over a 3 minute period. After stirring for 1 hour under ice-cooling (0 to 5° C.), 1 ml of a saturated sodium hydrogencarbonate aqueous solution was added to the reaction mixture. The mixture was extracted with 10 ml of butyl acetate, and the organic phase was washed with 2 ml of a 5% sodium chloride aqueous solution. Separately, 1 ml of butyl acetate was put into a 20 ml two-necked flask and heated to 110° C., and the above extract was added thereto dropwise over a 10 minute period. During the addition nitrogen was evolved vigorously. The reaction mixture was stirred at 100° C. for 4 hours. The butyl acetate was evaporated under reduced pressure, and the residue was purified by column chromatography to give 95 mg (99%) of the title compound. Optical purity: 99.9%e.e. or higher $^1$H-NMR (200 MHz, CDCl$_3$, δ ppm): 7.4–7.2 (m, 5H), 6.14 (bs, 1H), 5.7–5.5 (m, 1H), 5.10 (s, 2H), 4.8–4.6 (m, 1H), 3.7–3.2 (m, 4H).

$^{13}$C-NMR (50 MHz, CDCl$_3$, δ ppm): 159.78, 156.85, 136.18, 128.43, 128.09, 127.90, 75.34, 66.78, 43.58, 42.67.

The optical purity was measured on an (R)-MTPA amide derivative of the product by HPLC under the following conditions.

Column: Cosmosil 5SL (4.6 mm×250 mm), produced by Nacalai Tesque Inc.

Solvent: hexane/diethyl ether=3/7 (by volume)

Flow rate: 1.0 ml/min

Detection: 254 nm

REFERENCE EXAMPLE 4

Synthesis of methyl (2S,3R)-2-(N-benzoylamino)methyl-3-hydroxybutyrate

In a 100 ml autoclave was put a solution of 2.5 g (10 mmol) of methyl-2-(N-benzoylamino)methyl-3-oxobutyrate and 173 mg (0.102 mmol) of Ru$_2$Cl$_4$((R)-BINAP)$_2$.NEt$_3$ in 17.5 ml of methylene chloride, and the mixture was stirred at 50° C. under a hydrogen pressure of 10000 kPa for 20 hours. The solvent was removed by evaporation under reduced pressure, and the residue was purified by column chromatography to furnish 2.25 g (90%) of the title compound. Optical purity: 98%e.e.

$^1$H-NMR (200 MHz, CDCl$_3$, δ ppm): 7.8–7.4 (m, 5H), 7.02 (bs, 1H), 4.2–4.1 (m, 1H), 4.1–4.0 (m, 1H), 3.73 (s, 3H), 3.7–3.5 (m, 1H), 2.7–2.5 (m, 1H), 1.26 (d, J=6.3 Hz, 3H).

The optical purity of the product was determined on its (R)-MTPA ester by HPLC under the following conditions.

Column: Develosil 100-3 (4.6 mm×250 mm), manufactured by Nomura Kagaku K.K.

Solvent: hexane/diethyl ether=9/1 (by volume)

Flow rate: 1.0 ml/min

Detection: 254 nm

EXAMPLE 7

Synthesis of (2S,3R)-2-(N-benzoylamino)methyl-3-hydroxybutanohydrazide

In a 100 ml flask were put 3.80 g (15.1 mmol) of the methyl (2S,3R)-2-(N-benzoylamino)methyl-3-hydroxybutyrate (optical purity: 98%e.e.) obtained in Reference Example 4, 38 ml of methanol, and 4.54 g (90.74 mmol) of hydrazine monohydrate and heated under reflux for 10 hours in a nitrogen stream. The reaction mixture was cooled to 5° C., at which it was stirred for 1 hour. The precipitated crystals were collected by filtration and washed with 10 ml of diethyl ether to afford 2.35 g (62%) of the title compound. Melting point: 185.4° C. Optical purity: >99.9%.e.e $^1$H-NMR (200 MHz, CD$_3$OD, δ ppm): 7.8–7.7 (m, 2H), 7.6–7.3 (m, 3H), 3.92 (dq, J=8.2, 6.2 Hz, 1H), 3.79 (dd, J=4.8, 13.6 Hz, 1H), 3.63 (dd, J=8.2, 13.6 Hz, 1H), 2.49 (dd, =4.8, 8.2, 8.2 Hz, 1H), 1.19 (d, J=6.2 Hz, 3H).

The optical purity of the product was determined as follows. An acetic-acid solution (1 ml) of 50 mg (0.20 mmol) of the (2S,3R)-2-(N-benzoylamino)methyl-3-hydroxybutanohydrazide was cooled to 5° C., and 21 mg (0.30 mmol) of sodium nitrite was added to the solution. The reaction mixture was stirred at room temperature (22 to 24° C.) for 1 hour, followed by heating to 80° C., at which the reaction mixture was stirred for 1 hour. The acetic acid was removed by evaporation under reduced pressure, and the resulting crude product was converted to its (R)-MTPA amide derivative, which was analyzed by HPLC under the following conditions.

Column: Cosmosil 5SL (4.6 mm×250 mm), produced by Nacalai Tesque Inc.

Solvent: diethyl ether

Flow rate: 1.0 ml/min

Detection: 254 nm

EXAMPLE 8

Synthesis of (5R,4R)-5-methyl-4-(N-benzoylamino)methyl-2-oxazolidinone

In a 50 ml two-necked flask were put 412 mg (5.97 mmol) of sodium nitrite and 2 ml of water in a nitrogen streams, and a solution of 1.00 g (3.98 mmol) of the (2S,3R)-2-(N-benzoylamino)methyl-3-hydroxybutanohydrazide (optical purity: >99.9%.e.e) obtained in Example 7 in 6 ml of acetic acid was added thereto over 5 minutes while cooling with ice (0 to 5° C.). Separately, 1 ml of water was put in a 50 ml two-necked flask and heated to 50° C. in a nitrogen stream, and the above prepared reaction mixture was added thereto dropwise over 10 minutes. The resulting reaction mixture was stirred at 50° C. for 2 hours. Water was evaporated under reduced pressure, and 10 ml of butyl acetate was added to the residue, followed by filtration to remove sodium acetate. The separated sodium acetate was washed with two 5 ml portions of butyl acetate, and the washings were combined with the mother liquor. Butyl acetate was removed from the mother liquor under reduced pressure, and residue was purified by column chromatography to furnish 451 mg (48%) of the title compound. Melting point: 156.7° C. Optical purity: 99.9%.e.e. or higher.

$^1$H-NMR (200 MHz, CDCl$_3$, δ ppm): 7.9–7.7 (m, 2H), 7.6–7.3 (m, 3H), 6.99 (bs, 1H), 4.74 (dq, J=7.0, 6.6 Hz, 1H), 4.1–3.8 (m, 2H), 3.2–3.0 (m, 1H), 1.39 (d, J=6.6 Hz, 3H).

$^{13}$C-NMR (50 MHz, CDCl$_3$, δ ppm): 168.42, 160.36, 133.73, 131.66, 128.42, 127.30, 75.62, 54.97, 40.32, 14.35.

The optical purity was measured on an (R)-MTPA amide derivative of the product by HPLC under the following conditions.

Column: Cosmosil 5SL (4.6 mm×250 mm), produced by Nacalai Tesque Inc.
Solvent: diethyl ether
Flow rate: 1.0 ml/min
Detection: 254 nm

REFERENCE EXAMPLE 5

Synthesis of methyl (S)-3-hydroxy-3-phenylpropionate

In a 1 liter autoclave was charged a mixture of 0.84 g of (1.0 mmol) of $Ru_2Cl_4((R)\text{-Tol-BINAP})_2.NET_3$, 178 g (1.00 mol) of methyl benzoylacetate, and 500 ml of methanol, and the mixture was stirred at 50° C. under a hydrogen pressure of 1000 kPa for 16 hours. The solvent was evaporated under reduced pressure, and the residue was distilled under reduced pressure (99° C./100 Pa.) to yield 171 g (95%) of the title compound as liquid. Optical purity: 87%e.e.

$^1$H-NMR (200 MHz, $CDCl_3$, δ ppm): 7.5–7.2 (m, 5H), 5.2–5.0 (m, 1H), 3.71 (s, 3H), 3.29 (bs, 1H), 2.77 (dd, J=9.2, 16.3 Hz, 1H), 2.70 (dd, J=3.8, 16.3 Hz, 1H).

The measurement of optical purity was made under the following conditions.
Column: Chiralcel OD-H (4.6 mm×250 mm), manufactured by Daicel Chemical Industries, Ltd.
Solvent: hexane/isopropyl alcohol=95/5 (by volume)
Flow rate: 1.0 ml/min
Detection: 254 nm

EXAMPLE 9

Synthesis of (S)-3-hydroxy-3-phenylpropionohydrazide

In a 1 liter four-necked flask were charged 200 g (1.11 mol) of methyl (S)-3-hydroxy-3-phenylpropionate (optical purity: 87%e.e.), 77.8 g (1.56 mol) of hydrazine monohydrate, and 400 ml of methanol, and the mixture was heated at 70° C. for 3 hours. The reaction mixture was cooled to 5° C. with ice-water, followed by filtration. The collected crystals were dissolved in 4.7 liter of methanol while hot and cooled to 5° C. The crystals thus precipitated were collected by filtration and dried to give 148 g (74%) of the title compound. Melting point: 179.5° C. Optical purity: >99.9%e.e.

$^1$H-NMR (200 MHz, $D_2O$, δ ppm): 7.5–7.2 (m, 5H), 5.1–5.0 (m, 1H), 2.69 (dd, J=8.2, 14.2 Hz, 1H), 2.59 (dd, J=6.0, 14.2 Hz, 1H).

$^{13}$C-NMR (50 MHz, $CDCl_3$, δ ppm): 172.28, 142.56, 129.20, 128.65, 126.32, 71.11, 43.30.

The optical purity of the product was determined as follows. A mixture of 100 mg (0.55 mmol) of the (S)-3-hydroxy-3-phenylpropionohydrazide, 5 ml of pyridine, and 2 ml of ethyl acetate and stirred at room temperature for 3 hours. The reaction mixture was poured into water and extracted with ethyl acetate. The ethyl acetate layer was washed once with a 1N hydrochloric acid aqueous solution and twice with a 5% aqueous solution of sodium chloride, and dried over anhydrous sodium sulfate. The solvent was evaporated. The resultant crude product weighing 0.25 g was analyzed under the following conditions. The optical purity was 99.9%e.e. or higher.
Column: Chiralcel OD-H (4.6 mm×250 mm), manufactured by Daicel Chemical Industries, Ltd.
Solvent: hexane/isopropyl alcohol=7/3 (by volume)
Flow rate: 1.0 ml/min
Detection: 210 nm

EXAMPLE 10

Synthesis of (R)-5-phenyl-2-oxazolidinone

In a 1 liter four-necked flask were put 150 g (0.83 mol) of (S)-3-hydroxy-3-phenylpropionohydrazide (optical purity: >99.9%e.e.), 150 g (1.44 mol) of 35% concentrated hydrochloric acid, 220 ml of water, and 100 ml of ethyl acetate. After cooling to 5° C., a solution of 57.5 g (0.83 mol) of sodium nitrite in 80 ml of water was added thereto dropwise at 5° C. over a 1 hour period, followed by stirring at that temperature for 30 minutes. The aqueous layer of the reaction mixture was extracted with 100 ml of ethyl acetate, and the extract was combined with the ethyl acetate layer of the reaction mixture. The combined ethyl acetate extract was washed twice with a 5% sodium chloride aqueous solution. The ethyl acetate layer was added dropwise to 100 ml of hot water at 100° C. thereby to conduct thermal decomposition and to recover the ethyl acetate. After the addition, the residue was cooled to room temperature, 200 ml of ethyl acetate added, and the mixture dried over anhydrous sodium sulfate. The solvent was evaporated to give 123.5 g of a crude product, which was dissolved in a mixed solvent of 150 ml of water and 90 ml of methanol. The solution was cooled to 5° C. to yield crystals of (R)-5-phenyl-2-oxazolidinone (113.1 g, 83%). Melting point: 96.4° C. Optical purity: >99.9%e.e..

$^1$H-NMR (200 MHz, $CDCl_3$, δ ppm): 7.5–7.3 (m, 5H), 5.64 (t, J=8.2 Hz, 1H), 5.14 (bs, 1H), 3.99 (dd, J=8.2, 8.6 Hz, 1H), 3.55 (d, J=8.2 Hz, 8.6 Hz, 1H).

$^{13}$C-NMR (50 MHz, $CDCl_3$, δ ppm): 162.16, 140.57, 129.91, 129.83, 126.81, 79.36, 49.30.

The measurement of optical purity was made under the following conditions.
Column: Chiralcel OD-H (4.6 mm×250 mm), manufactured by Daicel Chemical Industries, Ltd..
Solvent: hexane/isopropyl alcohol=95/5 (by volume)
Flow rate: 1.0 ml/min
Detection: 210 nm

REFERENCE EXAMPLE 6

Synthesis of Ethyl (R)-4-Chloro-3-Hydroxybutyrate

In a 200 ml autoclave were charged 40.0 g (0.24 mol) of ethyl 4-chloro-3-oxobutyrate, 20 mg of $Ru_2Cl_4((S)\text{-Tol-BINAP})_2.NEt_3$, and 40 ml of ethanol, and reaction was conducted at 100° C. under a hydrogen pressure of 300 KPa for 5 hours. After the solvent was removed, the reaction mixture was distilled (60° C./200 Pa.) to give 30.3 g of the title compound. Optical purity: 95%e.e.

REFERENCE EXAMPLE 7

Synthesis of Ethyl (R)-4-Azido-3-Hydroxybutyrate

In a 200 ml four-necked flask were charged 20.0 g (0.12 mol) of ethyl (R)-4-chloro-3-hydroxybutyrate, 15.6 g (0.24 mol) of sodium azide and 80 ml of DMF, and the reaction mixture was stirred for 24 hours at a reaction temperature of about 100° C. After cooling the reaction mixture, the reaction mixture was diluted with 100 ml of toluene, washed with 50 ml of water, and concentrated to give 16.5 g (79%) of the title compound.

REFERENCE EXAMPLE 8

Synthesis of Ethyl (R)-4-Azido-3-Acetoxybutyrate

In a 100 ml four-necked flask were charged 5.0 g (28.8 mmol) of ethyl (R)-4-azido-3-hydroxybutyrate, 3.5 g (34.6 mmol) of triethylamine, 0.11 g (0.900 mmol) of 4-dimethylaminopyridine and 50 ml of tetrahydrofuran, and after the mixture was cooled to 0° C., 2.50 g (31.8 mmol) of acetyl chloride was slowly added thereto dropwise in a nitrogen stream. After the addition, the reaction mixture was further stirred at room temperature overnight, and then the solvent was distilled under reduced pressure to give 4.94 g of a concentrate. The concentrate was subjected to column chromatography (ethyl acetate/hexane=1/10 by volume) to obtain 4.50 g (73%) of the title compound.

REFERENCE EXAMPLE 9

Synthesis of Ethyl (R)-4-Acetylamino-3-Hydroxybutyrate

In a 200 ml autoclave were charged 4.50 g (20.9 mmol) of ethyl (R)-4-azido-3-acetoxybutyrate, 0.02 g of 5% Pd—C, and 5 ml of ethyl acetate, and the mixture was stirred at room temperature under a hydrogen pressure of 1000 KPa overnight. The catalyst was removed for concentration to give 3.20 g (81%) of the title compound.

EXAMPLE 11

Synthesis of (R)-4-Acetylamino-3-Hydroxybutanohydrazide

A 5.00 g (26.4 mmol) of ethyl (R)-4-acetylamino-3-hydroxybutyrate (optical purity: 95%e.e.) was dissolved in 20 ml of methanol, and 2.00 g (39.6 mmol) of hydrazine monohydrate was added thereto dropwise at room temperature. After the addition, the mixture was heated to 65° C. and then stirred overnight. After the mixture was cooled to room temperature, 20 ml of methanol was added thereto and crystallization was carried out at 10° C. to give 3.90 g (84%) of the title compound. Melting point: 177.5° C. Optical purity: >99.9%e.e.

$^1$HNMR (500 MHz, $CD_3SOCD_3$, δppm): 1.81 (s, 3H), 2.07 (dd, J=8.0, 14.2 Hz, 1H), 2.14 (dd, J=4.8, 14.2 Hz, 1H), 2.97–3.06 (m, 1H), 3.06–3.11 (m, 1H), 3.86 (bs, 1H), 4.14 (bs, 2H), 4.77 (d, J=4.4 Hz, 1H), 7.69 (bs, 1H), 8.85 (bs, 1H)

$^{13}$CNMR (126 MHz, $CD_3OD$, δppm): 22.54, 40.37, 46.17, 68.59, 172.81, 173.73

The optical purity of the product was measured as follows. An acetic acid solution (1 ml) of 36 mg (0.19 mmol) of the resulting (R)-4-acetylamino-3-hydroxybutanohydrazide was cooled to 5° C., and 19 mg (0.28 mmol) of sodium nitrite was added. The reaction mixture was stirred at room temperature (22 to 24° C.) for 1 hour and then heated up to 80° C., at which the mixture was further stirred for 1 hour. The acetic acid was removed by evaporation under reduced pressure. The resulting crude product was converted to its 4-chlorobenzoylamide derivative and analyzed by HPLC under the following conditions.

Column: CHIRALPAC-AD (4.6 mm×250 mm), produced by Daicel Chemical Industries, Ltd.

Solvent: hexane/2-propanol=9/1 (by volume)

Flow rate: 1.0 ml/min

Detection: 254 nm

EXAMPLE 12

Synthesis of (S)-5-Acetylaminomethyl-2-Oxazolidinone 14 ml of water was added to 3.50 g (20.0 mmol) of (R)-4-acetylamino-3-hydroxybutanohydrazide (optical purity: >99.9%e.e.), and the mixture was cooled to 0° C. Then, 2.29 g (22.0 mmol) of 35% HCL was added thereto dropwise over 10 min, and an aqueous solution of 1.52 g (22.0 mmol) of sodium nitrite dissolved in 3.5 ml of water was further added thereto dropwise slowly. After the reaction mixture was stirred for 1 hour at that temperature, the thus prepared reaction mixture was added to 10 ml of warm water (50° C.) dropwise over 2 hours. After the addition, the mixture was further stirred for 1 hour, water was then removed therefrom, and 30 ml of methanol was further added thereto for desalting to give 3.30 g of a crude product. The crude product was then subjected to crystallization with 10 ml of ethanol to give 2.75 g (87%) of the title compound. Melting point: 137.5° C. Optical purity: >99.9%e.e.

$^1$HNMR (500 MHz, $CD_3SOCD_3$, δppm): 1.84 (s, 3H), 3.14–3.18 (m, 1H), 3.29 (t, J=5.7 Hz, 2H), 3.49 (t, J=8.8 Hz, 1H), 4.52–4.58 (m, 1H), 7.32 (bs, 1H), 8.05 (bs, 1H)

$^{13}$CNMR (126 MHz, $CD_3OD$, δppm): 22.15, 41.46, 42.43, 73.91, 158.30, 169.55

The product was converted to its 4-chlorobenzoylamide derivative, which was analyzed by HPLC under the following conditions.

Column: CHIRALPAC-AD (4.6 mm×250 mm), produced by Daicel Chemical Industries, Ltd.

Solvent: hexane/2-propanol=9/1 (by volume)

Flow rate: 1.0 ml/min

Detection: 254 nm

REFERENCE EXAMPLE 10

Synthesis of Ethyl (R)-4-Azido-3-Hexanoyloxybutyrate

In a 100 ml four-necked flask were charged 6.0 g (34.6 mmol) of ethyl (R)-4-azido-3-hydroxybutyrate, 4.2 g (41.5 mmol) of triethylamine, 0.12 g (1.04 mmol) of 4-dimethylaminopyridine, and 60 ml of tetrahydrofuran and the mixture was cooled to 0° C. 5.10 g (38.1 mmol) of hexanoyl chlrodie was slowly added thereto dropwise in a nitrogen stream. After the addition, the reaction mixture was stirred at a room temperature for 5 hours, and then 14 ml of 5% HCL was added thereto. After the liquid separation, the mixture was washed thrice with 30 ml of 5% aqueous solution of sodium chloride and then concentrated to give 8.75 g (93%) of the title compound.

REFERENCE EXAMPLE 11

Synthesis of Ethyl (R)-4-Hexanoylamino-3-Hydroxybutyrate

In a 200 ml autoclave were charged 8.50 g (29.5 mmol) of ethyl (R)-4-azido-3-hexanoyloxybutyrate, 0.20 g of 5% Pd—C, and 16 ml of ethyl acetate, and the mixture was stirred at room temperature under a hydrogen pressure of 1000 KPa. for 7 hours. The catalyst was removed for concentration to give 7.07 g (87%) of the title compound.

EXAMPLE 13

Synthesis of (R)-4-Hexanoylamino-3-Hydroxybutanohydrazide

A 6.50 g (24.9 mmol) of ethyl (R)-4-hexanoylamino-3-hydroxybutyrate (optical purity: 95%e.e.) was dissolved in 26 ml of methanol, and 1.87 g (37.3 mmol) of hydrazine monohydrate was added thereto dropwise at room temperature. After the addition, the mixture was heated to 65° C. and then stirred for 2 hours. After the mixture was cooled to room temperature, stirring was conducted overnight to give 4.09 g (66%) of the title compound as a crystal. Melting point: 172.5° C. Optical purity: >99.9%e.e.

$^1$HNMR (500 MHz, CD$_3$SOCD$_3$, δppm): 0.86 (t, J=7.0 Hz, 3H), 1.21–1.28 (m, 4H), 1.47–1.52 (m, 2H), 2.03–2.08 (m, 3H), 2.13 (dd, J=4.8, 14.1 Hz, 1H), 3.00–3.03 (m, 1H), 3.07–3.10 (m, 1H), 3.84–3.87 (m, 1H), 4.13 (bs, 2H), 4.76 (d, J=4.9 Hz, 1H), 7.62 (bs, 1H), 8.86 (bs, 1H)

$^{13}$CNMR (126 MHz, CD$_3$OD, δppm): 14.26, 23.43, 26.66, 32.56, 37.04, 40.43, 46.06, 68.69, 172.83, 176.76

The optical purity of the product was measured as follows. An acetic acid solution (1 ml) of 47 mg (0.19 mmol) of the resulting (R)-4-hexanoylamino-3-hydroxybutanohydrazide was cooled to 5° C., and 19 mg (0.28 mmol) of sodium nitrite was added. The reaction mixture was stirred at room temperature (22 to 24° C.) for 1 hour and then heated up to 80° C., at which the mixture was further stirred for 1 hour. The acetic acid was removed by evaporation under reduced pressure. The resulting crude product was converted to its MTPA amide derivative and analyzed by HPLC under the following conditions.

Column: Cosmosil 5SL (4.6 mm×250 mm), produced by Nacalai Tesque Inc.
Solvent: hexane/2-propanol=95/5 (by volume)
Flow rate: 1.0 ml/min
Detection: 254 nm

EXAMPLE 14

Synthesis of (S)-5-Hexanoylaminomethyl-2-Oxazolidinone 33 ml of water was added to 2.50 g (10.1 mmol) of (R)-4-hexamoylamino-3-hydroxybutanohydrazide (optical purity: >99.9%e.e.), and the mixture was cooled to 0° C. A 1.16 g (11.1 mmol) of 35% HCl was added thereto dropwise over 10 min, and then an aqueous solution of 0.77 g (11.1 mmol) of sodium nitrite dissolved in 2.5 ml of water was further added thereto dropwise slowly. After the reaction mixture was stirred for 2 hour at that temperature, the thus prepared reaction mixture was added to 10 ml of warm water (50° C.) dropwise over 1 hour. After the addition, the mixture was further stirred for 1 hour, cooled to room temperature, and then extracted thrice with a 20 ml portion of ethyl acetate. The extracted ethyl acetate was then concentrated to give 2.05 g of a crude product. The crude product was subjected to column chromatography (ethyl acetate/hexane=1/1 by volume) to obtain 0.96 g (85%) of the title compound. Melting point: 124.1° C. Optical purity: >99.9%e.e.

$^1$HNMR (500 MHz, CD$_3$SOCD$_3$, δppm): 0.91 (t, J=7.2 Hz, 3H), 1.26–1.36 (m, 4H), 1.52–1.58 (m, 2H), 2.10–2.17 (m, 2H), 3.18–3.20 (m, 3H), 3.53 (t, J=8.3 Hz, 1H), 4.63–4.58 (m, 1H), 7.34 (bs, 1H), 7.97 (bs, 1H)

$^{13}$CNMR (126 MHz, CD$_3$OD, δppm): 13.45, 21.49, 24.60, 30.57, 35.00, 41.31, 42.33, 73.96, 158.29, 172.57

The product was converted to its MTPA amide derivative, which was analyzed by HPLC under the following conditions.

Column: Cosmosil 5SL (4.6 mm×250 mm), produced by Nacalai Tesque Inc.
Solvent: hexane/2-propanol=95/5 (by volume)
Flow rate: 1.0 ml/min
Detection: 254 nm

REFERENCE EXAMPLE 12

Synthesis of Ethyl (R)-4-t-Butoxycarbonylamino-3-Hydroxybutyrate

In a 200 ml autoclave were charged 4.90 g (28.2 mmol) of Ethyl (R)-4-azido-3-hexanoyloxybutyrate, 0.25 g of 5% Pd—C, 6.47 g (29.6 mmol) of (Boc)$_2$O and 5 ml of ethyl acetate, and the mixture was stirred at room temperature under a hydrogen pressure of 10 torr. for 8 hours. The catalyst was removed for concentration to give 5.26 g (75%) of the title compound.

EXAMPLE 15

Synthesis of (R)-4-t-Butoxycarbonylamino-3-Hydroxybutanohydrazide

A 6.50 g (26.1 mmol) of ethyl (R)-4-t-butoxycarbonylamino-3-hydroxybutyrate (optical purity: 95%e.e.) was dissolved in 26 ml of methanol, and 1.96 g (39.1 mmol) of hydrazine monohydrate was added thereto dropwise at room temperature. After the addition, the mixture was heated to 65° C. and then stirred for 5 hours. After the mixture was cooled to room temperature, stirring was conducted overnight to give 4.27 g (70%) of the title compound. Melting point: 143.6° C. Optical purity: >99.9%e.e.

$^1$HNMR (500 MHz, CD$_3$SOCD$_3$, δppm): 1.38 (s, 9H), 2.04 (dd, J=8.2, 14.2 Hz, 1H), 2.14 (dd, J=4.5, 14.2 Hz, 1H), 2.87–2.98 (m, 2H), 3.80–3.87 (m, 1H), 4.11 (bs, 1H), 4.69 (d, J=5.0 Hz, 1H), 6.53 (bs, 1H), 8.84 (bs, 1H)

$^{13}$CNMR (126 MHz, CD$_3$OD, δppm): 28.73, 40.29, 47.05, 68.98, 80.72, 158.62, 172.96

The optical purity of the product was measured as follows. An acetic acid solution (1 ml) of 44 mg (0.19 mmol) of the resulting (R)-4-butoxycarbonylamino-3-hydroxybutanohydrazide was cooled to 5° C., and 19 mg (0.28 mmol) of sodium nitrite was added. The reaction mixture was stirred at room temperature (22 to 24° C.) for 1 hour and then heated up to 80° C., at which the mixture was further stirred for 1 hour. The acetic acid was removed by evaporation under reduced pressure. The resulting crude product was converted to its MTPA amide derivative and analyzed by HPLC under the following conditions.

Column: Inertsi SIL 100-5 (4.6 mm×250 mm), produced by GL Sciences Inc.
Solvent: hexane/2-propanol=95/5 (by volume)
Flow rate: 0.5 ml/min
Detection: 254 nm

EXAMPLE 16

Synthesis of (S)-5-t-Butoxycarbonylaminomethyl-2-Oxazolidinone 10 ml of water was added to 2.00 g (8.57 mmol) of (R)-4-t-butoxycarbonylamino-3-hydroxybutanohydrazide (optical purity: >99.9%e.e.), and the mixture was cooled to 0° C. A 0.89 g (8.57 mmol) of 35% HCl was added thereto dropwise over 10 min, and then an aqueous solution of 0.59 g (8.57 mmol) of sodium nitrite dissolved in 2.0 ml of water was further added thereto dropwise slowly. After the reaction mixture was stirred for 1 hour at that temperature, the thus prepared reaction mixture was added to 10 ml of warm water (50° C.) dropwise over 1 hour. After the addition, the mixture was further stirred for 1 hour, cooled to room temperature, and then extracted thrice with a 20 ml portion of ethyl acetate. The extracted ethyl acetate was then concentrated to give 1.06 g of a crude product. The crude product was subjected to column chromatography (ethyl acetate) to obtain 0.96 g (52%) of the title compound. Melting point: 115.5° C. Optical purity: >99.9%e.e.

$^1$HNMR (500 MHz, CD$_3$SOCD$_3$, δppm): 1.43 (s, 9H), 3.18–3.24 (m, 3H), 3.5 (t, J=8.8 Hz, 1H), 4.54–4.59 (m,1H), 6.49 (bs, 1H), 7.32 (bs, 1H)

$^{13}$CNMR (126 MHz, CD$_3$OD, δppm): 28.69, 43.99, 44.12, 76.98, 80.36, 158.44, 161.81

The product was converted to its MTPA amide derivative, which was analyzed by HPLC under the following conditions.

Column: Inertsi SIL 100-5 (4.6 mm×250 mm), produced by GL Sciences Inc.

Solvent: hexane/2-propanol=95/5 (by volume)

Flow rate: 0.5 ml/min

Detection: 254 nm

REFERENCE EXAMPLE 13

Synthesis of Methyl (2S,3S)-2-Benzyl-3-Hydroxybutyrate

In a 500 ml autoclave were put 100 g (861 mmol) of methyl acetoacetate, 50 mg (0.0592 mmol) of Ru$_2$Cl$_4$ ((S-BINAP)$_2$.NEt$_3$ and 100 ml of methanol in a nitrogen stream, and hydrogenation was carried out at 50° C. under a hydrogen pressure of 500 KDa for 45 hours. After the reaction was terminated, methanol was collected, and the resulting mixture was distilled under reduced pressure to give 91.56 g of methyl (S)-3-hydroxybutyrate (65° C./1300 Pa., 96%e.e.).

Subsequently, in a 50 ml flask were charged 3.3 g (30.0 mmol) of diisopropylamine and 10 ml of tetrahydrofuran, and 16.6 ml (24.9 mmol) of n-butyllithium 1.5M hexane solution was added thereto dropwise on an ice bath in a nitrogen stream. The mixture was then stirred for 1 hour at that temperature. The reaction mixture was further cooled to −40° C., and 1.40 g (11.9 mmol) of methyl (S)-3-hydroxybutyrate prepared as above was added thereto dropwise. After the mixture was stirred for 0.5 hour, 3.00 g (17.5 mmol) of benzyl bromide dissolved in 6 ml of hexamethylphosphoramide was added thereto dropwise at −10° C. or lower temperature. After the addition, the temperature was heated up to 0° C., and the mixture was stirred for 15 min. The resulting mixture was then poured into an ice water, and was extracted with ethyl acetate. The ethyl acetate layer was concentrated to give 3.90 g of a crude product. The crude product was subjected to column chromatography (hexane/ethyl acetate=4/1 by volume) to obtain 1.50 g (61%) of the title compound (anti/syn=98/2).

EXAMPLE 17

Synthesis of (2S,3S)-2-Benzyl-3-Hydroxybutanohydrazide

A 0.70 g (3.36 mmol) of methyl (2S,3S)-2-benzyl-3-hydroxybutyrate (optical purity: 96%e.e.; anti/syn=98/2) was dissolved in 1 ml of 2-propanol, and 0.34 g (6.72 mmol) of hydrazine monohydrate was added thereto dropwise at room temperature. After the addition, the mixture was refluxed for 8 hours, and then stirred overnight to obtain a concentrate. The obtained concentrate was crystallized by using a mixed solvent of ethyl acetate and hexane to give 0.45 g (64%) of the title compound. Melting point: 167.1° C. Optical purity: >99.9%e.e. anti/syn>99/1

$^1$HNMR (500 MHz, CD$_3$SOCD$_3$, δppm): 1.10 (d, J=6.4 Hz, 3H), 2.38–2.42 (m, 1H), 2.73 (dd, J=4.8, 13.6 Hz, 1H), 2.83 (dd, J=9.8, 13.6 Hz, 1H), 3.65–3.75 (m, 1H), 4.08 (s, 2H), 4.51 (d, J=5.6 Hz, 1H), 7.12–7.15 (m, 3H), 7.21–7.24 (m, 2H), 8.77 (bs, 1H)

$^{13}$CNMR (126 MHz, CD$_3$OD, δppm): 20.95, 33.32, 52.80, 66.88, 125.53, 127.83, 128.54, 140.07, 172.06

The optical purity and the diastereomer ratio of the product were measured as follows. An acetic acid solution (1 ml) of 40 mg (0.19 mmol) of the resulting (2S,3S)-2-benzyl-3-hydroxybutanohydrazide was cooled to 5° C., and 19 mg (0.28 mmol) of sodium nitrite was added. The reaction mixture was stirred at room temperature (22 to 24° C.) for 1 hour and then heated up to 80° C., at which the mixture was further stirred for 1 hour. The acetic acid was removed by evaporation under reduced pressure. The resulting crude product was analyzed by GLC under the following conditions.

Optical purity:

Column: CHIRALSIL-DEX CB (0.25 mm×25 m), produced by Chrompack Inc.

Injection temp.: 200° C.

Column temp.: 165° C.

Detection temp.: 250° C.

Diastereomer ratio:

Column: Neutral Bond-I (0.25 mm×30 m), produced by GL Sciences Inc.

Injection temp.: 200° C.

Column temp.: 150–180° C.

Detection temp.: 250° C.

Rise of temp.: 2° C./min.

EXAMPLE 18

Synthesis of (4S,5S)-4-Benzyl-5-Methyl-2-Oxazolidinone 5.5 ml of water was added to 0.50 g (2.40 mmol) of (2S,3S)-2-benzyl-3-hydroxybutanohydrazide (optical purity: >99.9%e.e.; anti/syn>99/1), and the mixture was cooled to 0° C. A 0.30 g (2.88 mmol) of 35% HCl was added thereto dropwise. After the addition, then an aqueous solution of 0.20 g (2.88 mmol) of sodium nitrite dissolved in 1.0 ml of water was further added thereto dropwise slowly. After the reaction mixture was stirred for 1 hour at that temperature, the thus prepared reaction mixture was added to 10 ml of warm water (50° C.) dropwise over 0.5 hour. After the addition, the mixture was further stirred for 1 hour, cooled to room temperature, and then extracted thrice with a 10 ml portion of toluene. The extracted toluene was then concentrated to give 0.33 g of a crude product. The crude product was subjected to column chromatography (hexane/ethyl acetate=1/1 by volume) to obtain 0.25 g (52%) of the title compound. Melting point: 115.5° C. Optical purity: >99.9%e.e. anti/syn>99/1

$^1$HNMR (500 MHz, CD$_3$SOCD$_3$, δppm): 1.07 (d, J=6.3 Hz, 3H), 2.73 (dd, J=7.2, 13.6 Hz, 1H), 2.83 (dd, J=5.6, 13.6 Hz, 1H), 3.53–3.59 (m, 1H), 4.23–4.26 (m, 1H), 7.22–7.23 (m, 3H), 7.27–7.30 (m, 2H), 7.59 (bs, 1H)

$^{13}$CNMR (126 MHz, CD$_3$OD, δppm): 19.97, 40.16, 59.53, 76.38, 126.46, 128.30, 129.32, 136.47, 157.69

The resulting crude product was analyzed by GLC under the following conditions for measurement of the optical purity and the diastereomer ratio.

Optical purity:
  Column: CHIRALSIL-DEX CB (0.25 mm×25 m), produced by Chrompack Inc.
  Injection temp.: 200° C.
  Column temp.: 165° C.
  Detection temp.: 250° C.
Diastereomer ratio:
  Column: Neutral Bond-I (0.25 mm×30 m), produced by GL Sciences Inc.
  Injection temp.: 200° C.
  Column temp.: 150–180° C.
  Detection temp.: 250° C.
  Rise of temp.: 2° C./min.

What is claimed is:

1. A process for preparing an optically active oxazolidinone derivative represented by formula (I):

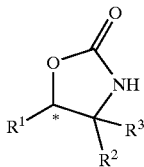

wherein $R^1$ represent a lower alkyl group having 1 to 4 carbon atoms, a phenyl group, a methoxymethyl group, a benzyloxymethyl group, a benzyloxycarbonylaminomethyl group which may have a substituent or substituents on the benzene ring thereof an acylaminomethyl group having 3 to 10 carbon atoms, or an alkyloxycarbonylaminomethyl group having 3 to 6 carbon atoms; $R^2$ and $R^3$, which may be the same or different, each represent a hydrogen atom, a lower alkyl group having 1 to 4 carbon atoms, a phenyl group, an acetylaminomethyl group, a benzoylaminomethyl group, or a benzyl group; and * indicates an asymmetric carbon atom, comprising allowing hydrazine to react on an optically active acid ester having a hydroxyl group at the 3-position which is represented by formula (II):

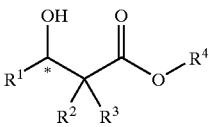

wherein $R^1$, $R^2$, $R^3$, and * are as defined above: and $R^4$ represents a lower alkyl group having 1 to 4 carbon atoms, to give an optically active hydrazide having a hydroxyl group at the 3-position which is represented by formula (III):

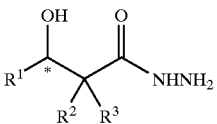

wherein $R^1$, $R^2$, $R^3$, and * are as defined above, and subjecting the optically active hydrazide to Curtius rearrangement to prepare the compound of formula I.

2. A process according to claim 1, wherein said optically active hydrazide having a hydroxyl group at the 3-position is recrystallized to increase its purity.

3. A process according to claim 1, wherein said optically active acid ester having a hydroxyl group at the 3-position is a compound represented by formula (II) wherein $R^1$ represents a methyl group, a phenyl group, a methoxymethyl group, a benzyloxymethyl group, a benzyloxycarbonylaminomethyl group, an acetylaminomethyl group, a hexanoylaminomethyl group, or a t-butoxycarbonylaminomethyl group; $R^2$ and $R^3$ both represent a hydrogen atom, or one of $R^2$ and $R^3$ represents a hydrogen atom with the other representing an acetylaminomethyl group, a benzoylaminomethyl group, or a benzyl group; and $R^4$ represents a lower alkyl group having 1 to 4 carbon atoms.

* * * * *